United States Patent
Brehm et al.

(10) Patent No.: US 6,358,046 B1
(45) Date of Patent: *Mar. 19, 2002

(54) CLASS II OR III MALOCCLUSION CORRECTION APPLIANCE

(75) Inventors: Waldemar Brehm, La Costa; Steven Prins, Atascadero; Steven M. Huff, San Diego, all of CA (US)

(73) Assignee: Ortho Organizers, San Marcos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/718,863

(22) Filed: Nov. 21, 2000

Related U.S. Application Data

(63) Continuation-in-part of application No. 09/459,003, filed on Dec. 10, 1999, now Pat. No. 6,162,051.

(51) Int. Cl.[7] .................................................. A61C 3/00
(52) U.S. Cl. ........................................... 433/19; 433/22
(58) Field of Search ............................. 433/18, 19, 21, 433/22

(56) References Cited

U.S. PATENT DOCUMENTS

| | | | |
|---|---|---|---|
| 4,462,800 A | * 7/1984 | Jones | 433/19 |
| 4,795,342 A | 1/1989 | Jones | 433/19 |
| 5,562,445 A | 10/1996 | DeVincenzo et al. | 433/19 |
| 5,738,514 A | 4/1998 | DeVincenzo et al. | 433/19 |
| 5,853,291 A | 12/1998 | DeVincenzo et al. | 433/176 |
| 5,980,247 A | 11/1999 | Cleary | 433/19 |

FOREIGN PATENT DOCUMENTS

| | | |
|---|---|---|
| FR | 1165755 | 10/1958 |
| FR | 2702141 A | 9/1994 |
| IT | 608117 | 9/1960 |

* cited by examiner

*Primary Examiner*—John J. Wilson
(74) *Attorney, Agent, or Firm*—Fulwider Patton Lee & Utecht, LLP

(57) ABSTRACT

The orthodontic appliance for correction of Class II or III malocclusions attaches to the maxillary arch on an archwire adjacent to the first molar and to the mandibular arch on an archwire in the cuspid or bicuspid area, and applies a low continuous force through the use of two plunger piston type devices, whether the mouth is open or closed. Dual acting piston cylinders are connected together, with first and second piston connecting rods extending in opposing directions from the piston cylinders. A first mounting element is provided at the exterior end of the first piston connecting rod for mounting the first piston connecting rod to at least one of the maxillary teeth, and a second mounting element is provided at the exterior end of the second piston connecting rod for mounting the second piston connecting rod to at least one of the mandibular teeth, for providing a continuous biasing force between the maxillary and mandibular teeth for treatment of malocclusions.

7 Claims, 4 Drawing Sheets

FIG. 7
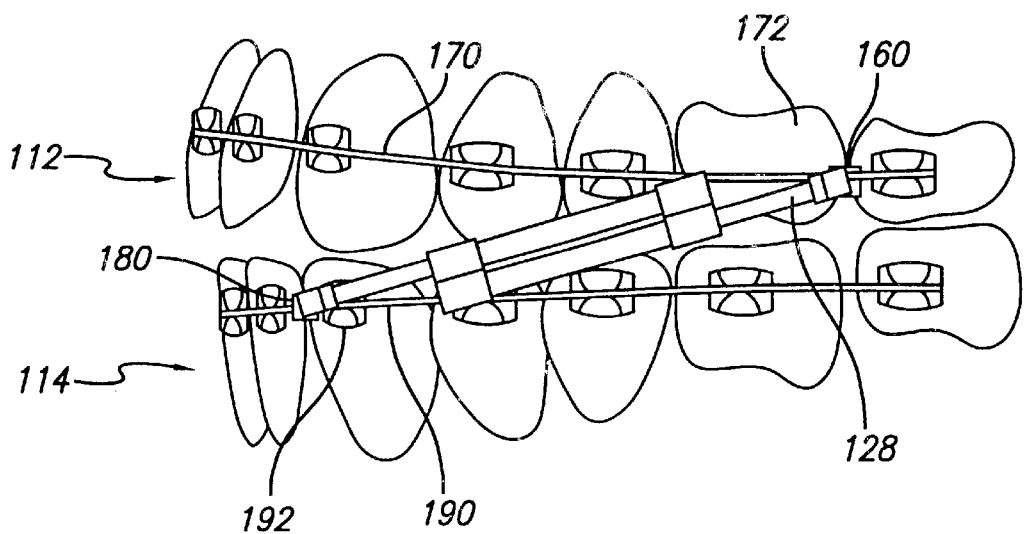
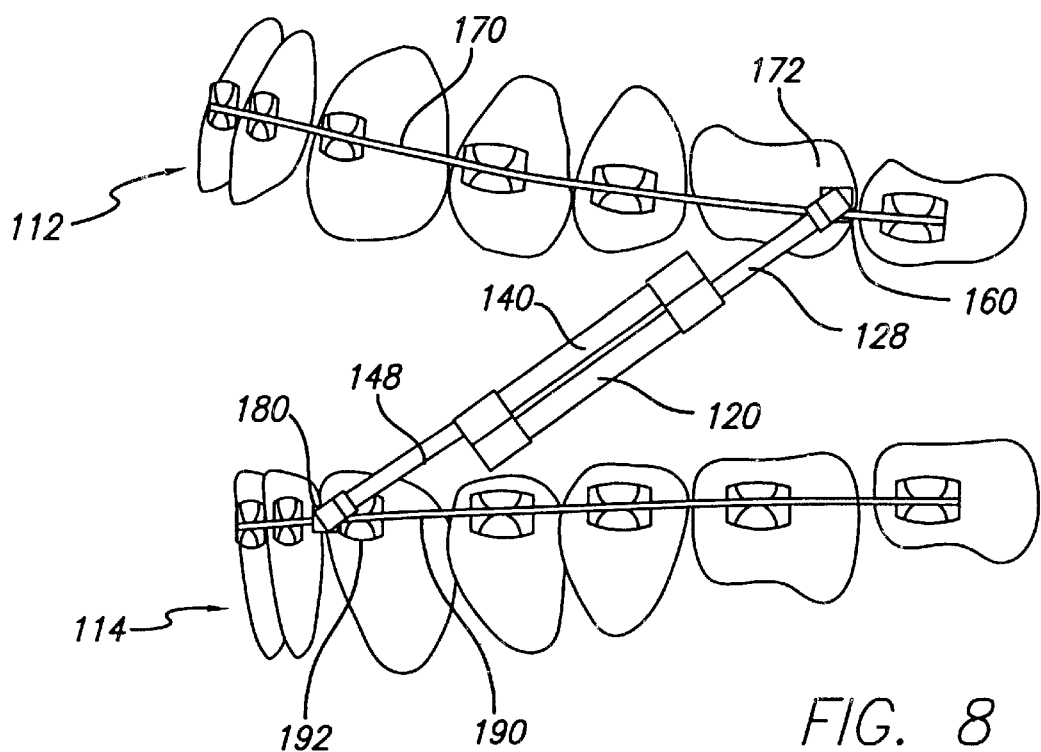
FIG. 8

CLASS II OR III MALOCCLUSION CORRECTION APPLIANCE

RELATED APPLICATIONS

This is a continuation in part of Ser. No. 09/459,003 filed Dec. 10, 1999 now U.S. Pat. No. 6,162,051.

BACKGROUND OF THE INVENTION

1. Field of the Invention

This invention relates generally to orthodontic appliances, and more particularly concerns a Class II or III malocclusion correction device that applies low continuous force through the use of dual plunger piston type devices, whether the mouth is open or closed. The appliance attaches to the maxillary arch at the first molar and to the mandibular arch on the archwire in the cuspid or bicuspid area, either unilaterally or bilaterally.

2. Description of Related Art

Orthodontic appliances, such as brackets, buccal tubes and the like, are typically applied to teeth by adhering the appliances to the surface of the teeth. Such appliances typically include archwire portions for receiving an archwire and ligature elastic bands to provide corrective forces to straighten and reposition the teeth. Headgear mounting tubes can also be attached to the maxillary arch at about the first molar, for the mounting of corrective headgear to straighten and reposition the teeth. Such orthodontic appliances typically include a base portion adapted to conform to the shape of the teeth to which they are applied.

A Class I malocclusion typically occurs when the bite is satisfactory in that the upper or maxillary teeth line up with the lower or mandibular teeth, but individual teeth are crooked, crowded or turned. A Class II malocclusion, also called an "overbite," or "buck teeth," occurs when the upper teeth project beyond the lower teeth. A Class III malocclusion, also called an "underbite," occurs when the lower teeth project beyond the upper teeth. Orthodontic appliances can be used to exert a force between an individual's upper and lower sets of teeth to aid in correction of such malocclusions. While coil springs have been used to apply force for adjustment of malocclusions, coil springs can be uncomfortable for patients and can require the wearing of embarrassing and uncomfortable headgear, are subject to wear and breakage, and can limit the degree of a patient's jaw movement.

There thus remains a need for a malocclusion correction device that is ideal for a non-compliant patient, allows flexibility in jaw movement, can be used on either left or right sides of a patient's teeth, and can even be used unilaterally. It would be desirable to provide a malocclusion correction device for correction of Type II or III malocclusions, that eliminates the need for headgear, aids in midline correction, does not limit the patient's range of motion of the lower jaw, and applies a constant force whether the patient's mouth is open or closed, providing for a more predictable treatment time. The present invention meets these needs.

SUMMARY OF THE INVENTION

Briefly, and in general terms, the present invention provides for an orthodontic appliance for correction of Class II or III malocclusions, that allows a full range of motion and flexibility of jaw movement, applies a low continuous force through the use of two plunger piston type devices, whether the mouth is open or closed. The appliance of the present invention attaches to the maxillary arch at the first molar and to the mandibular arch on the archwire in the cuspid or bicuspid area, either unilaterally or bilaterally. The appliance can be used for either the left and right sides of the teeth of a patient, and can be used on one side alone, if desired. The appliance of the present invention eliminates the need for the use of headgear for correction of Class II or III malocclusions, and can used as an aid in midline corrections. With the orthodontic appliance of the invention, the duration of a course of orthodontic treatment for correction of Class II or III malocclusions can be more predictable than was heretofore possible.

The present invention accordingly provides for an orthodontic appliance for correction of Class II or III malocclusion of maxillary teeth and mandible teeth, with dual piston cylinders connectable between the maxillary teeth and mandible teeth. The orthodontic appliance comprises a first piston cylinder and a second piston cylinder connected together, with each piston cylinder having first and second ends. The first piston cylinder includes a first piston connecting rod slidably connected within the first piston cylinder and extending from the first end of the first piston cylinder, and the first piston cylinder biases the first piston connecting rod in a direction along the longitudinal axis. The second piston cylinder includes a second piston connecting rod slidably connected within the second piston cylinder and extending from the first end of the second piston cylinder, and the second piston cylinder biases the second piston connecting rod in a direction along the longitudinal axis of the second piston connecting rod, with the exterior ends of the first and the second piston connecting rods extending in opposing directions. In a presently preferred aspect, a first archwire is connected to the maxillary teeth, and a second archwire is connected to the mandible teeth. A first mounting element is connected to the exterior end of the first piston connecting rod for mounting the first piston connecting rod to the first archwire connected to the maxillary teeth, and a second mounting element is connected to the exterior end of the second piston connecting rod for mounting the second piston connecting rod to the second archwire connected to the mandibular teeth.

In a presently preferred embodiment, the first piston connecting rod is biased to extend toward the exterior end of the first piston connecting rod, and the second piston connecting rod is biased to extend toward the exterior end of the second piston connecting rod. In another presently preferred aspect of the invention, the first mounting element is connected to the exterior end of the first piston connecting rod by a ball and socket joint so as to be rotatable with respect to the first piston cylinder, and the second mounting element is connected to the exterior end of the second piston connecting rod by a ball and socket joint so as to be rotatable with respect to the second piston cylinder. In another presently preferred aspect, the first and second mounting elements comprise locking fasteners connectable to the first and second archwires, respectively.

In one currently preferred embodiment, the first piston cylinder comprises a first piston cylinder housing, a first compression spring disposed in the first piston cylinder dwelling, the interior end of the first piston connecting rod being connected to the first compression spring, the first piston connecting rod being slidable within the first piston cylinder housing along the longitudinal axis of the first piston connecting rod, the first compression spring biasing the first piston connecting rod to extend away from the first compression spring; and the second piston cylinder comprises a second piston cylinder housing, a second compression spring disposed in the second piston cylinder housing, the interior end of the second piston connecting rod being connected to the second compression spring, the second piston connecting rod being slidable within the second piston cylinder housing along the longitudinal axis of the second piston connecting rod, the second compression spring biasing the second piston connecting rod to extend away from the second compression spring.

These and other aspects and advantages of the invention will become apparent from the following detailed description and the accompanying drawings, which illustrate by way of example the features of the invention.

BRIEF DESCRIPTION OF THE DRAWINGS

FIG. 7 is an illustration of a deployment of the orthodontic appliance of FIG. 5 between maxillary and mandibular sets of teeth, with the mouth closed; and FIG. 8 is an illustration of a deployment of the orthodontic appliance of FIG. 5 between maxillary and mandibular sets of teeth, with the mouth open.

DETAILED DESCRIPTION OF THE PREFERRED EMBODIMENTS

Figure 3:
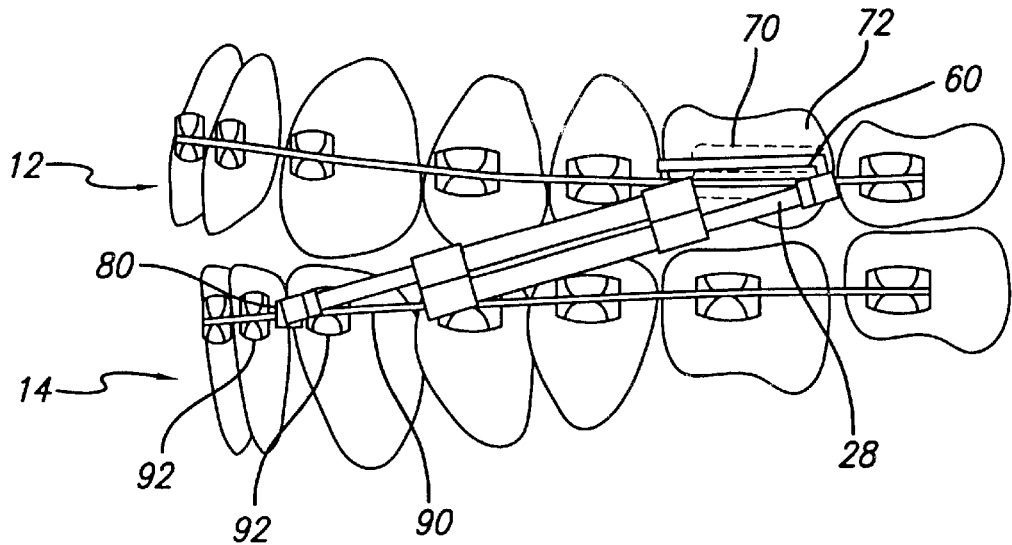
FIG. 3 is an illustration of a deployment of the orthodontic appliance of FIG. 1 between maxillary and mandibular sets of teeth, with the mouth closed.
Figure 4:
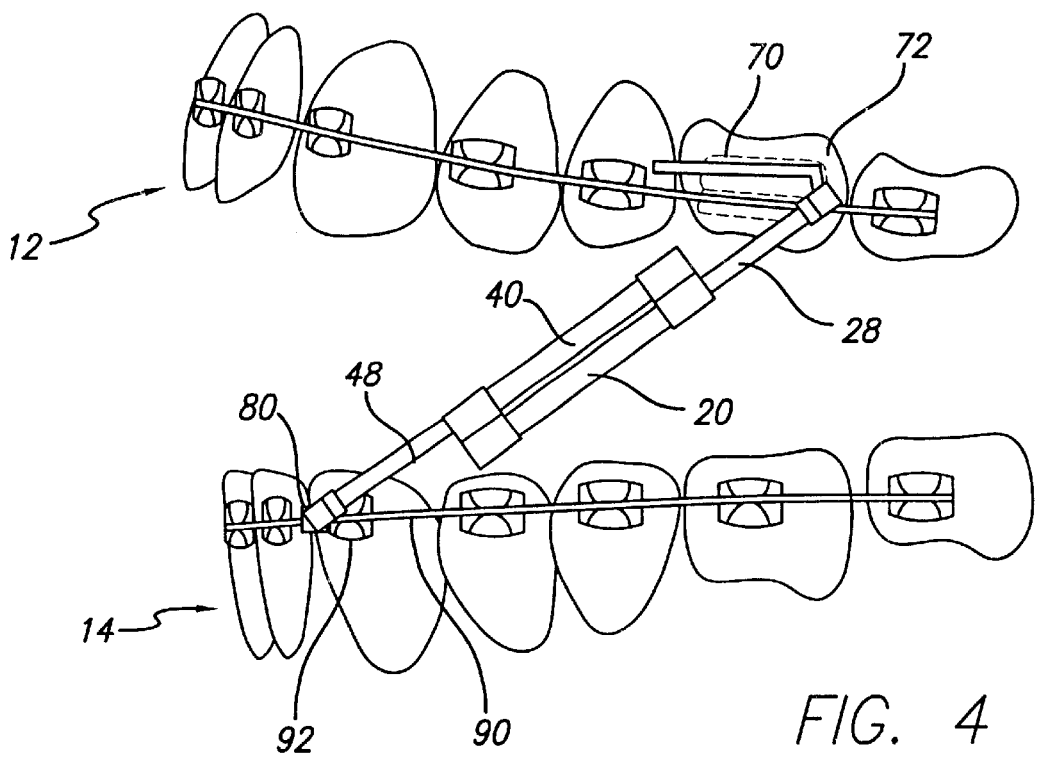
FIG. 4 is an illustration of a deployment of the orthodontic appliance of FIG. 1 between maxillary and mandibular sets of teeth, with the mouth open.

As is illustrated in the drawings, the invention is embodied in an orthodontic appliance 10 for correction of Class II or III malocclusion of maxillary teeth 12 and mandibular teeth 14, as is illustrated in FIGS. 3 and 4. The orthodontic appliance advantageously employs dual acting pistons 16, 18 connected together in tandem, to bias the maxillary and mandibular teeth in the desired directions for treatment of a malocclusion.

Figure 1:
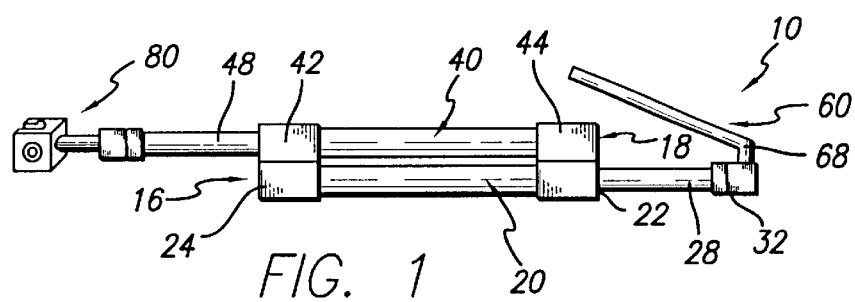
FIG. 1 is a plan view of the orthodontic appliance according to the present invention.
Figure 2:
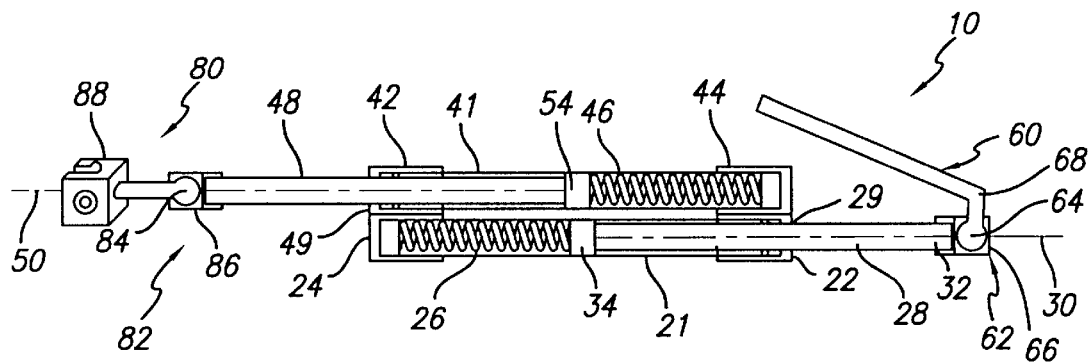
FIG. 2 is a sectional view of the orthodontic appliance of FIG. 1.

Referring to FIGS. 1 and 2, the dual acting pistons include a first piston cylinder 20 having a housing 21 with a first end 22, and a second end 24, with a first compression spring 26 disposed in the first piston cylinder. Connected to the first compression spring is a first piston connecting rod 28 extending from a slot 29 in the first end of the first piston cylinder, the first piston connecting rod having a longitudinal axis 30, an exterior end 32, and an interior end 34. The interior end of the first connecting rod is connected to the first compression spring, and is slidable within the piston cylinder housing relative to the first piston cylinder along the longitudinal axis of the first piston connecting rod.

The dual acting pistons also include a second piston cylinder 40 having a housing 41 with a first end 42 and a second end 44, with a second compression spring 46 disposed in the second piston cylinder. A second piston connecting rod 48 is connected to the second compression spring, and extends from a slot 49 in the first end of the second piston cylinder, the second piston connecting rod having a longitudinal axis 50, an exterior end 52, and an interior end 54. The interior end of the second connecting rod is connected to the second compression spring, and the second piston connecting rod is slidable within the second piston cylinder housing along the longitudinal axis of the second piston connecting rod.

The second piston cylinder is preferably connected adjacent to the first piston cylinder, with the first end of the first piston cylinder adjacent to the second end of the second piston cylinder, and the second end of the first piston cylinder adjacent to the first end of the second piston cylinder, with the exterior ends of the first and the second piston connecting rods extending in opposing directions. Alternatively, the first and second piston cylinders could be connected end to end. In a presently preferred embodiment, the first compression spring biases the first piston connecting rod to extend away from the first compression spring, and the second compression spring biases the second piston connecting rod to extend away from the second compression spring, as depicted in the figures, to bias the first and second connecting rods apart; although the first and second compression springs could alternatively be configured to bias the first and second connecting rods together.

A first mounting element 60 is connected to the exterior end of the first piston connecting rod for mounting the first piston connecting rod to at least one of the maxillary teeth. In a currently preferred aspect, the first mounting element is connected to the exterior end of the first piston connecting rod by a ball and socket joint 62, including a ball 64 disposed within a socket 66 at the exterior end of the first piston connecting rod, so that the first piston connecting rod is rotatable with respect to the first piston cylinder. In another presently preferred aspect, the first mounting element comprises an annealed wire 68 connectable to a headgear buccal tube 70, shown in phantom in FIGS. 3 and 4, to allow bending of the annealed wire gingivally and distally, as needed for adjusting the orthodontic appliance for effectiveness and comfort. Such a headgear buccal tube is described in U.S. Pat. No. 6,053,729, which is incorporated by reference herein. As is illustrated in FIGS. 3 and 4, the first mounting element is preferably attached to at least one of the maxillary teeth, such as by adhesive, and is currently preferably attached to the maxillary arch at the first molar 72.

A second mounting element 80 is connected to the exterior end of the second piston connecting rod for mounting the second piston connecting rod to at least one of the mandibular teeth. In another presently preferred aspect, the second mounting element is connected to the exterior end of the second piston connecting rod by a ball and socket joint 82, including a ball 84 contained within a socket 86 at the exterior end of the second piston connecting rod, so that the second piston connecting rod is rotatable with respect to the second piston cylinder. In a presently preferred aspect, the second mounting element is a locking fastener 88, such as a clamp that can be a slotted member with an Allen screw, as illustrated, or a forked or bifurcated member, for example, that can be closed around an arch wire 90 as shown in FIGS. 3 and 4, or other appliance, and typically to be attached to the mandibular arch on an archwire connected to the teeth by orthodontic brackets 92, in the cuspid or bicuspid area. As is illustrated in FIGS. 3 and 4, the orthodontic appliance of the invention can thus be used for continuously biasing the mandibular teeth and jaw forward while continuously biasing the maxillary teeth and jaw backward to correct a Class II malocclusion, whether the mouth of the patient is open or closed.

In an other presently preferred embodiment illustrated in FIGS. 5–8, the invention is embodied in an orthodontic appliance 110 for correction of Class II or III malocclusion of maxillary teeth 112 and mandibular teeth 114, as is illustrated in FIGS. 7 and 8. The orthodontic appliance advantageously employs dual acting pistons 116, 118 connected together in tandem, to bias the maxillary and mandibular teeth in the desired directions for treatment of a malocclusion.

Figure 5:
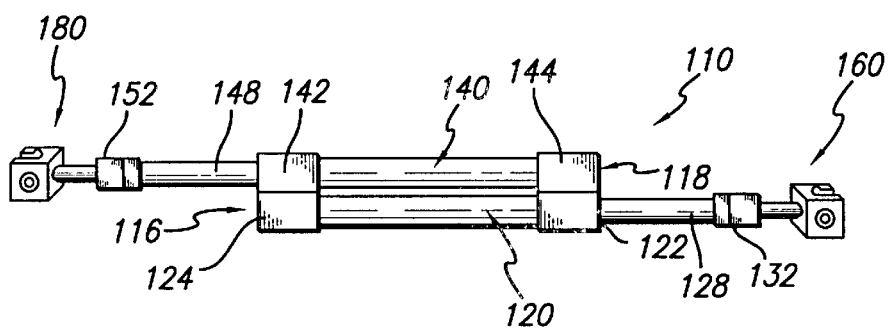
FIG. 5 is a plan view of an alternate embodiment of the orthodontic appliance according to the present invention.
Figure 6:
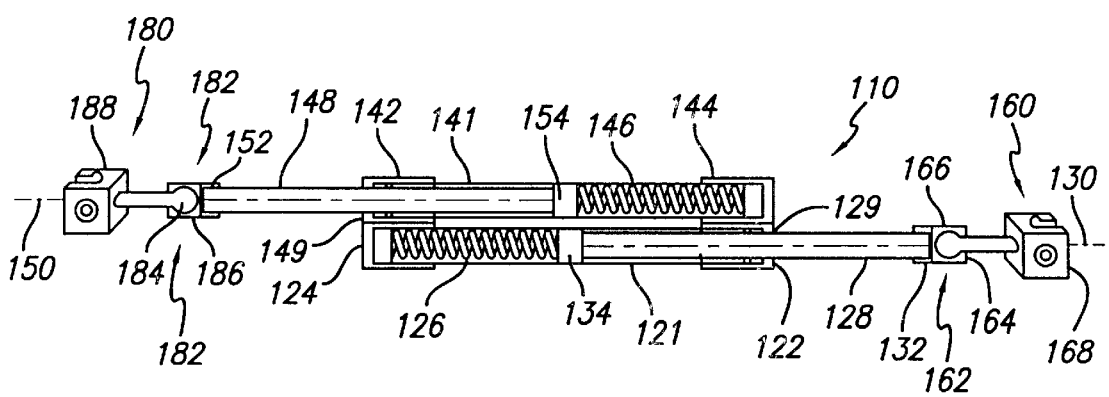
FIG. 6 is a sectional view of the orthodontic appliance of FIG. 5.

Referring to FIGS. 5 and 6, the dual acting pistons include a first piston cylinder 120 having a housing 121 with a first end 122, and a second end 124, with a first compression spring 126 disposed in the first piston cylinder. Connected to the first compression spring is a first piston connecting rod 128 extending from a slot 129 in the first end of the first piston cylinder, the first piston connecting rod having a longitudinal axis 130, an exterior end 132, and an interior end 134. The interior end of the first connecting rod is connected to the first compression spring, and is slidable within the piston cylinder housing relative to the first piston cylinder along the longitudinal axis of the first piston connecting rod.

The dual acting pistons also include a second piston cylinder 140 having a housing 141 with a first end 142 and a second end 144, with a second compression spring 146 disposed in the second piston cylinder. A second piston connecting rod 148 is connected to the second compression spring, and extends from a slot 149 in the first end of the second piston cylinder, the second piston connecting rod having a longitudinal axis 150, an exterior end 152, and an interior end 154. The interior end of the second connecting rod is connected to the second compression spring, and the second piston connecting rod is slidable within the second piston cylinder housing along the longitudinal axis of the second piston connecting rod.

The second piston cylinder is preferably connected adjacent to the first piston cylinder, with the first end of the first piston cylinder adjacent to the second end of the second piston cylinder, and the second end of the first piston cylinder adjacent to the first end of the second piston cylinder, with the exterior ends of the first and the second piston connecting rods extending in opposing directions. Alternatively, the first and second piston cylinders could be connected end to end. In a presently preferred embodiment, the first compression spring biases the first piston connecting rod to extend away from the first compression spring, and the second compression spring biases the second piston connecting rod to extend away from the second compression spring, as depicted in the figures, to bias the first and second connecting rods apart; although the first and second compression springs could alternatively be configured to bias the first and second connecting rods together.

A first mounting element 160 is connected to the exterior end of the first piston connecting rod for mounting the first piston connecting rod to at least one of the maxillary teeth. In a currently preferred aspect, the first mounting element is connected to the exterior end of the first piston connecting rod by a ball and socket joint 162, including a ball 164 disposed within a socket 166 at the exterior end of the first piston connecting rod, so that the first piston connecting rod is rotatable with respect to the first piston cylinder. In a presently preferred aspect, the first mounting element is a locking fastener 168, such as a clamp that can be a slotted member with an Allen screw, as illustrated, or a forked or bifurcated member, for example, that can be closed around an arch wire 170 as shown in FIGS. 7 and 8, or other appliance, and typically to be attached to the maxillary arch on an archwire connected to the teeth by orthodontic brackets 192, in the adjacent to the first molar 172.

A second mounting element 180 is connected to the exterior end of the second piston connecting rod for mounting the second piston connecting rod to at least one of the mandibular teeth. In another presently preferred aspect, the second mounting element is connected to the exterior end of the second piston connecting rod by a ball and socket joint 182, including a ball 184 contained within a socket 186 at the exterior end of the second piston connecting rod, so that the second piston connecting rod is rotatable with respect to the second piston cylinder. In a presently preferred aspect, the second mounting element is also a locking fastener 188, such as a clamp that can be a slotted member with an Allen screw, as illustrated, or a forked or bifurcated member, for example, that can be closed around an arch wire 190 as shown in FIGS. 7 and 8, or other appliance, and typically to be attached to the mandibular arch on an archwire connected to the teeth by orthodontic brackets 192, in the cuspid or bicuspid area. As is illustrated in FIGS. 7 and 8, the orthodontic appliance of the invention can thus be used for continuously biasing the mandibular teeth and jaw forward while continuously biasing the maxillary teeth and jaw backward to correct a Class II malocclusion, whether the mouth of the patient is open or closed.

While the present invention has been described and shown as designed for use in moving the mandibular teeth and jaw forward while moving the maxillary teeth and jaw backward to correct a Class II malocclusion, it should be readily appreciated that the mounting of the device can be reversed and arranged to affix the second mounting element in the frontal area of the maxillary teeth, and to affix the first mounting element in the back area of the mandibular teeth, to reverse the direction of the force exerted on the maxillary and mandibular teeth, for correction of a Class III malocclusion.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An orthodontic appliance for correction of Class II or III malocclusion of maxillary teeth and mandible teeth, comprising:

a first piston cylinder having first and second ends, a first piston connecting rod slidably connected within said first piston cylinder and extending from said first end of said first piston cylinder, said first piston connecting rod having a longitudinal axis, an interior end and an exterior end, said first piston cylinder biasing said first piston connecting rod in a direction along said longitudinal axis;

a second piston cylinder having first and second ends, a second piston connecting rod slidably connected within said second piston cylinder and extending from said first end of said second piston cylinder, said second piston connecting rod having a longitudinal axis, an interior end and an exterior end, said second piston cylinder biasing said second piston connecting rod in a direction along said longitudinal axis, said second piston cylinder connected to said first piston cylinder, and said exterior ends of said first and said second piston connecting rods extending in opposing directions;

a first archwire for connecting to said maxillary teeth;

a second archwire for connecting to said mandible teeth;

a first mounting element connected to said exterior end of said first piston connecting rod for mounting said first piston connecting rod to said first archwire; and a second mounting element connected to said exterior end of said second piston connecting rod for mounting said second piston connecting rod to said second archwire.

2. The orthodontic appliance of claim 1, wherein said first piston connecting rod is biased to extend toward said exterior end of said first piston connecting rod, and said second piston connecting rod is biased to extend toward said exterior end of said second piston connecting rod.

3. The orthodontic appliance of claim 1, wherein said first piston cylinder comprises a first piston cylinder housing, a first compression spring disposed in said first piston cylinder dwelling, said interior end of said first piston connecting rod being connected to said first compression spring, said first piston connecting rod being slidable within said first piston cylinder housing along said longitudinal axis of said first piston connecting rod, said first compression spring biasing said first piston connecting rod to extend away from said first compression spring; and said second piston cylinder comprises a second piston cylinder housing, a second compression spring disposed in said second piston cylinder housing, said interior end of said second piston connecting rod being connected to said second compression spring, said second piston connecting rod being slidable within said second piston cylinder housing along said longitudinal axis of said second piston connecting rod, said second compression spring biasing said second piston connecting rod to extend away from said second compression spring.

4. The orthodontic appliance of claim 1, wherein said first mounting element is connected to said exterior end of said first piston connecting rod by a ball and socket joint so as to be rotatable with respect to said first piston cylinder.

5. The orthodontic appliance of claim 1, wherein said first mounting element comprises a locking fastener.

6. The orthodontic appliance of claim 1, wherein said second mounting element is connected to said exterior end of said second piston connecting rod by a ball and socket joint so as to be rotatable with respect to said second piston cylinder.

7. The orthodontic appliance of claim 1, wherein said second mounting element comprises a locking fastener.

* * * * *

UNITED STATES PATENT AND TRADEMARK OFFICE
CERTIFICATE OF CORRECTION

PATENT NO.   : 6,358,046 B1  
DATED        : March 19, 2002  
INVENTOR(S)  : Waldemar Brehm et al.

It is certified that error appears in the above-identified patent and that said Letters Patent is hereby corrected as shown below:

<u>Title page,</u>  
Under Item [75], Inventors:, change "Atascadero", to read -- San Luis Obispo --.  
Under Item [76], Inventors, change "Steven M. Huff", to read -- Stephen M. Huff --.

Signed and Sealed this

Ninth Day of July, 2002

Attest:

JAMES E. ROGAN  
Attesting Officer    Director of the United States Patent and Trademark Office